(12) United States Patent
Aoki et al.

(10) Patent No.: US 12,125,592 B2
(45) Date of Patent: Oct. 22, 2024

(54) DIAGNOSIS ASSISTANCE DEVICE, DIAGNOSIS ASSISTANCE METHOD, AND RECORDING MEDIUM

(71) Applicant: CASIO COMPUTER CO., LTD., Shibuya (JP)

(72) Inventors: Nobuhiro Aoki, Kokubunji (JP); Yoshiharu Houjou, Nerima (JP); Shigeki Mineo, Hino (JP); Junichi Takei, Nakano (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 463 days.

(21) Appl. No.: 17/314,166

(22) Filed: May 7, 2021

(65) Prior Publication Data

US 2021/0265060 A1 Aug. 26, 2021

Related U.S. Application Data

(63) Continuation of application No. PCT/JP2019/050179, filed on Dec. 20, 2019.

(30) Foreign Application Priority Data

Jan. 10, 2019 (JP) ................. 2019-002461

(51) Int. Cl.
*G16H 50/20* (2018.01)
*G06T 7/00* (2017.01)
(Continued)

(52) U.S. Cl.
CPC ........... *G16H 50/20* (2018.01); *G06T 7/0012* (2013.01); *G10L 15/08* (2013.01); *G16H 30/40* (2018.01); *G10L 2015/088* (2013.01)

(58) Field of Classification Search
CPC ........ G16H 50/20; G16H 30/40; G16H 30/20; G06T 7/0012; G10L 15/08; G10L 2015/088; A61B 5/00; A61B 10/00
See application file for complete search history.

(56) References Cited

U.S. PATENT DOCUMENTS

2008/0226151 A1* 9/2008 Zouridakis ............ G06T 7/0012
600/300
2008/0275315 A1* 11/2008 Oka ...................... A61B 5/445
705/3
(Continued)

FOREIGN PATENT DOCUMENTS

CN 108742703 A 11/2018
EP 2908281 A1 * 8/2015 ......... G06Q 30/0623
(Continued)

OTHER PUBLICATIONS

Varma, Mobile teledermatology for skin tumour screening, 2011, British Journal of Dermatology, pp. 939-941. (Year: 2011).*
(Continued)

*Primary Examiner* — Christopher L Gilligan
(74) *Attorney, Agent, or Firm* — Holtz, Holtz & Volek PC (57) ABSTRACT

A diagnosis assistance device includes at least one microphone that collects voice around an affected area, and at least one processor. The at least one processor determines, based on image data that is data of a captured image of the affected area, whether the affected area is malignant, and stores in a memory the voice collected by the microphone when determination is made that the affected area is malignant.

6 Claims, 6 Drawing Sheets

(51) Int. Cl.
*G10L 15/08* (2006.01)
*G16H 30/40* (2018.01)

(56) References Cited

U.S. PATENT DOCUMENTS

| | | | | |
|---|---|---|---|---|
| 2009/0198296 | A1* | 8/2009 | Sanghera | A61N 1/3956 607/5 |
| 2010/0036676 | A1* | 2/2010 | Safdi | G16H 15/00 705/2 |
| 2010/0317924 | A1* | 12/2010 | Sisko | A61B 1/00105 600/200 |
| 2014/0306992 | A1* | 10/2014 | Tsujimoto | G16H 70/60 345/632 |
| 2015/0223749 | A1 | 8/2015 | Park et al. | |
| 2018/0031817 | A1 | 2/2018 | Barral | |
| 2019/0231249 | A1* | 8/2019 | Dascalu | A61B 5/746 |
| 2021/0297635 | A1* | 9/2021 | Horiuchi | A61B 1/05 |

FOREIGN PATENT DOCUMENTS

| | | |
|---|---|---|
| JP | 2015152601 A | 8/2015 |
| WO | 2015012028 A1 | 1/2015 |
| WO | 2018005316 A1 | 1/2018 |

OTHER PUBLICATIONS

International Search Report (ISR) (and English language translation thereof) dated Mar. 10, 2020 issued in International Application No. PCT/JP2019/050179.
Written Opinion dated Mar. 10, 2020 issued in International Application No. PCT/JP2019/050179.
Chinese Office Action (and an English language translation thereof) dated Jun. 7, 2023, issued in counterpart Chinese Application No. 2019800693152.
Extended European Search Report (EESR) dated Sep. 14, 2022, issued in counterpart European Application No. 19908642.2.

* cited by examiner

DIAGNOSIS ASSISTANCE DEVICE, DIAGNOSIS ASSISTANCE METHOD, AND RECORDING MEDIUM

CROSS-REFERENCE TO RELATED APPLICATION

This application claims the benefits of Japanese Patent Application No. 2019-002461, filed on Jan. 10, 2019 and International Application No. PCT/JP2019/050179, filed on Dec. 20, 2019, the entire disclosures of which are incorporated by reference herein.

TECHNICAL FIELD

The present disclosure relates to a diagnosis assistance device, a diagnosis assistance method, and a recording medium.

BACKGROUND ART

Conventionally, tumor dissemination may be induced when performing a partial biopsy instead of a total excision biopsy to observe a melanoma (malignant melanoma) or the like. As such, it is known that such techniques are of no benefit to patients. Accordingly, such observations rely on the sight of trained physicians.

A device and an observation method whereby pigmentation of skin of a predetermined size is magnified and imaged using a digital camera are known as one type of dermoscopy for non-invasively observing a medical condition without performing a partial biopsy. Such a device includes a dermoscope module attached to a digital camera and enables the pigmentation state of skin tissue from the skin surface to near the dermis to be searched by observing each of light reflected from the skin surface and light that reflects after reaching the dermis. Moreover, as such a digital dermoscope, an observation system has been proposed in which a polarizing filter is used to enable the observation of each of the light reflected from the skin surface and from inside the dermis. With this conventional dermoscope, high-intensity light rays are used in order to detect so-called diffuse reflection, that is, the reflection of light that has passed through the epidermis and reached the dermis (for example, see Unexamined Japanese Patent Application Publication No. 2015-152601).

SUMMARY

A diagnosis assistance device of the present disclosure includes at least one microphone capable of collecting voice around an affected area, and at least one processor. The at least one processor is configured to determine, based on image data that is data of a captured image of the affected area, whether the affected area is malignant, and store in a memory the voice collected by the at least one microphone when determination is made that the affected area is malignant.

DESCRIPTION OF EMBODIMENTS

Hereinafter, a diagnosis assistance device and the like according to embodiments of the present disclosure are described while referencing the drawings. Note that, in the drawings, identical or corresponding components are marked with the same reference numerals.

Embodiment 1

A diagnosis assistance device according to Embodiment 1 includes a dermoscope, and can be used to observe medical conditions of patients. For example, the diagnosis assistance device can be used in the examination, observation, and/or treatment of pigment cell nevus, malignant melanoma, seborrheic keratoses, basal cell carcinoma, vascular lesions, Bowen's disease, and the like. With this dermoscope, a light source is used to irradiate a target area of the skin with light, reflected light from the skin surface covering the interior of the skin is reduced, and the target area is magnified and observed. As a result, inflammation, color, pigmentation, hair follicles, blood vessels, and the like inside the skin can be non-invasively visualized. When examining an affected area, a user (a physician or the like) of the diagnosis assistance device observes the affected area using the diagnosis assistance device. As a result, the examination process can be confirmed after the end of the examination and can be referenced when diagnosing.

Note that, in the present description, the terms "dermoscope" and "dermoscopy" are used to refer respectively to a skin examination magnifier (device) and skin examination by a magnifier or a use of a magnifier (action), in a manner similar to the usage of "microscope" (device) and "microscopy" (examination by a microscope or use of a microscope (method)).

Figure 1:
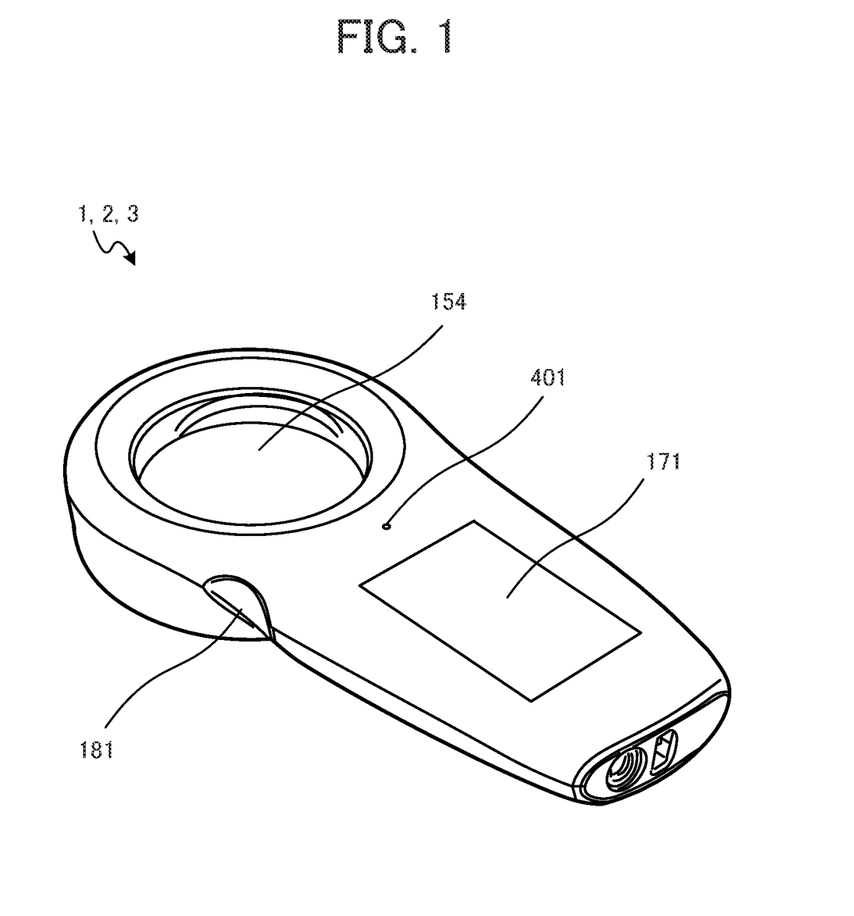
FIG. 1 is a back perspective view of a diagnosis assistance device according to Embodiment 1.
Figure 2:
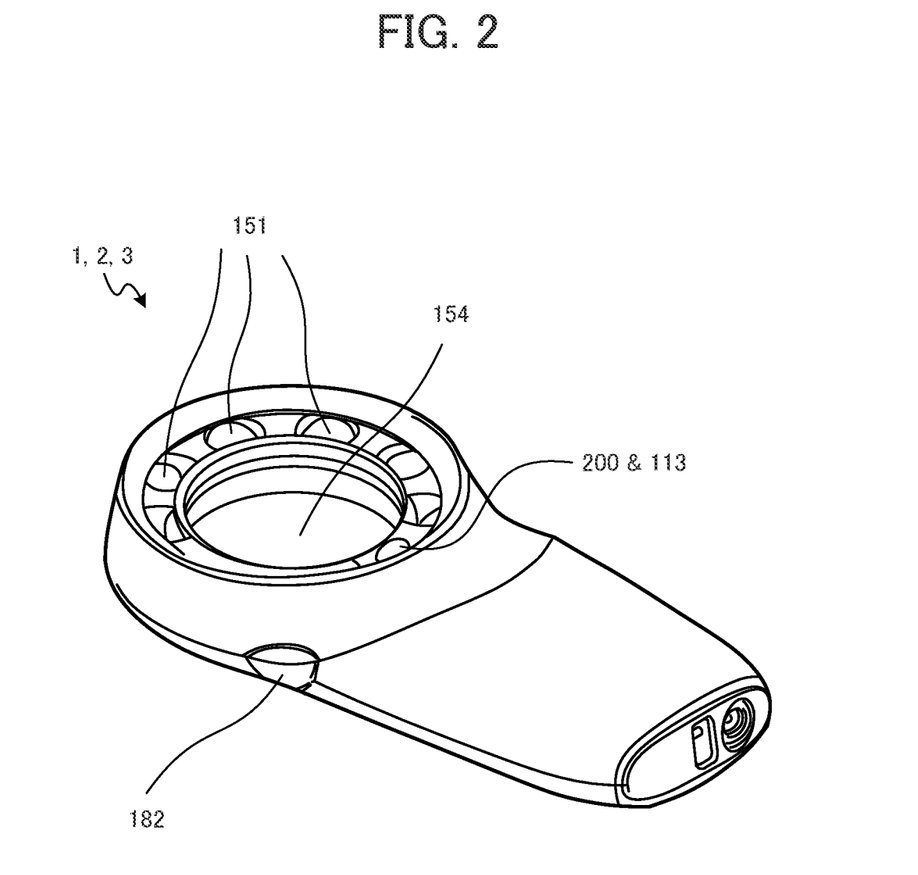
FIG. 2 is a front perspective view of the diagnosis assistance device according to Embodiment 1.

As illustrated in FIG. 1 and FIG. 2, a diagnosis assistance device 1 according to Embodiment 1 includes, in an upper portion, an observation lens 154. The observation lens 154 can be confirmed from the front surface and from the back surface of the diagnosis assistance device 1, but is disposed at a portion closer to the back surface side (sunken portion when viewed from the front). Additionally, as illustrated in FIG. 1, the diagnosis assistance device 1 includes, on the back surface, at least one microphone 401 and a display panel 171 and, on a left side surface when viewing the back surface, a light type switching button 181. Furthermore, as illustrated in FIG. 2, the diagnosis assistance device 1 includes, on the front surface, a lesion imaging lens 200, an imaging element 113, and light sources 151 and, on a left side surface when viewing the front surface, a power button 182. Note that, as described later, the light type switching button 181 is a button that switches the type, brightness, or the like of light of the light sources 151. The power button 182 is a button that turns the power of the diagnosis assistance device 1 ON and OFF. As illustrated in FIG. 1 and FIG. 2, the light type switching button 181 and the power button 182 are provided on side surfaces between the observation lens 154 and a handle portion. As such, the user of the diagnosis assistance device 1 can operate these buttons using the thumb or the like of the hand holding the diagnosis assistance device 1. Note that, in the present description, the front surface of the diagnosis assistance device 1 refers to the surface on which the light sources 151 are provided, and the back surface of the diagnosis assistance device 1 refers to the surface on the user side when the user observes an affected area. As illustrated in FIG. 1, the display panel 171 is provided in a portion on the handle side of the diagnosis assistance device 1, and the microphone 401 is provided between the observation lens 154 and the display panel 171. Due to this configuration, sound collection by the microphone 401 is not obstructed by the hand of the user holding the diagnosis assistance device 1, and the surrounding sound can be more easily collected.

As illustrated in FIG. 1 and FIG. 2, the user (physician or the like) of the diagnosis assistance device 1 can directly visually observe, through the observation lens 154 from the back surface of the diagnosis assistance device 1, an affected area present in the direction of the front surface of the diagnosis assistance device 1. At such a time, the type and brightness of the light of the light sources 151 provided on the front surface of the diagnosis assistance device 1 can be switched using the light type switching button 181. Additionally, the diagnosis assistance device 1 can acquire image data by imaging the affected area (lesion image) using the lesion imaging lens 200 and the imaging element 113.

As illustrated in FIG. 2, the imaging element 113 is provided together with the light sources 151 on an outer periphery of the portion where the observation lens 154 is attached. Additionally, the lesion imaging lens 200 is provided in a portion of the diagnosis assistance device 1 in front (on the surface side) of the imaging element 113. The diagnosis assistance device 1 can carry out dermoscopy imaging by using the imaging element 113 to capture an image of light from the direction of the front surface of the diagnosis assistance device 1 (reflected image of affected area) as a dermoscopy image magnified by the lesion imaging lens 200. Note that when an imaging optical system 111 (described later) also serves as the lesion imaging lens 200, it is not necessary to provide a lesion imaging lens.

The lesion imaging lens 200 functions as a magnifying lens that magnifies the affected area. The magnification power of the lesion imaging lens 200 is, for example, from 5-times to 30-times. The lesion imaging lens 200 may be implemented as any of a one double-sided convex lens, a lens in which two or a plurality of convex lenses are combined, one achromat lens, and a lens in which two or more achromat lenses are combined. Additionally, the lesion imaging lens 200 may be implemented as an aberration lens. Furthermore, the lesion imaging lens 200 may be obtained by incorporating an aspherical lens into a spherical lens to obtain excellent optical properties and reduce distortion. The lesion imaging lens 200 may further include an antireflection film, a color filter, or the like.

Figure 3:
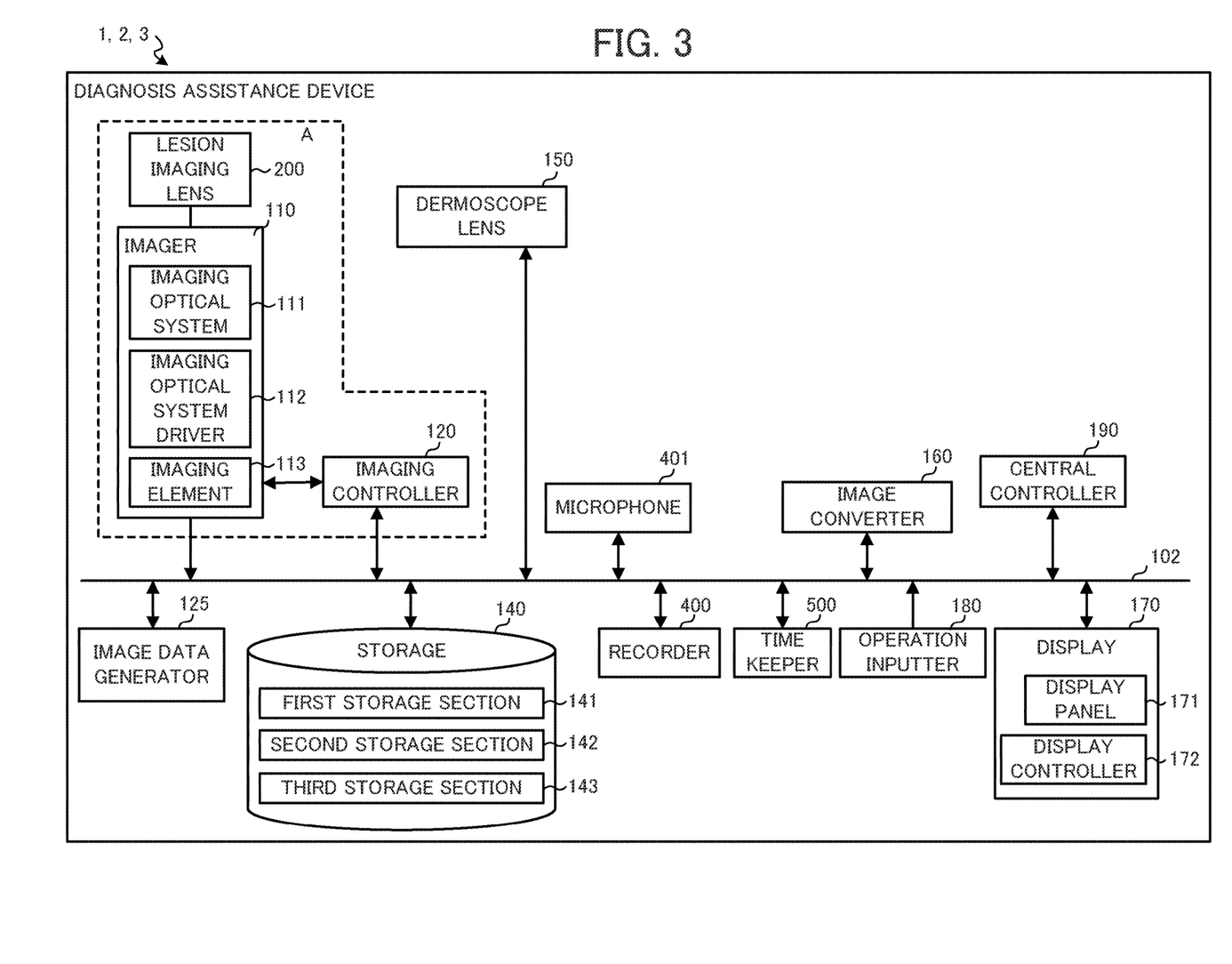
FIG. 3 is a block diagram illustrating a schematic configuration of the diagnosis assistance device according to Embodiment 1.

As illustrated in FIG. 3, the diagnosis assistance device 1 includes an imager 110, an imaging controller 120, an image data generator 125, a storage 140, an image converter 160, a display 170, an operation input device 180, a central controller 190, a sound recorder 400, a microphone 401, and a time keeper 500. These constituents are each commonly connected via a bus line 102, and are disposed in a housing of the diagnosis assistance device 1.

Note that, in FIG. 3, the dashed line region A illustrates the configuration of a diagnosis assistance device 1 with functions restricted to imaging lesions. The diagnosis assistance device 1 may further include a communicator for sending and receiving information to and from an external device (computer), thereby allowing some or all of the storage 140, the display 170, and the operation input device 180 to be transferred to the external device (a configuration is possible in which these constituents are provided on the external device side). In this case, as described later, an observation system is formed from the external device and the diagnosis assistance device 1. Note that, when forming the observation system, the configuration in which constituents are transferred to the external device may be expanded. For example, a portion or the entirety of the central controller 190 may be transferred to the external device.

The imager 110 includes an imaging optical system 111, an imaging optical system driver 112, and an imaging element 113. The imager 110 images the affected area. The imaging optical system driver 112 is constituted by an actuator such as a motor, and drives a diaphragm and a lens of the imaging optical system 111. The imaging element 113 converts, by photoelectric conversion, the reflected image of the affected area projected by the imaging optical system 111 to an electrical signal, and outputs the result as an image signal.

The imaging optical system 111 includes at least one of a zoom lens, a focus lens, and a diaphragm. When the imaging optical system 111 also includes the functions of the lesion imaging lens 200 such as when including a zoom lens capable of 30-times magnification, for example, it is not necessary to provide the diagnosis assistance device 1 with the lesion imaging lens 200 as described above. However, typically, it is preferable that a lesion imaging lens 200 for magnifying the affected area is provided separately from the imaging optical system 111. This is because providing the lesion imaging lens 200 eliminates the need to greatly increase the magnification power of the imaging optical system 111, which makes it possible to obtain excellent optical performance with little distortion. With the imaging optical system 111, the diaphragm and the lens are driven by the imaging optical system driver 112 on the basis of a control signal from the imaging controller 120 illustrated in FIG. 3, and a reflected image of the affected area, which is set to an appropriate brightness, is formed on the imaging element 113. The imaging element 113 converts the reflected image, formed by the imaging optical system 111, of the affected area to an electrical signal by photoelectric conversion, and outputs the result to the image data generator 125. The imaging element 113 is implemented as, for example, a charge coupled device (CCD) image sensor or a complementary metal oxide semiconductor (CMOS) image sensor.

The imaging controller 120 has a function for controlling the driving of the imaging element 113 to control the imaging of the affected area by the imager 110. Specifically, while not illustrated in the drawings, the imaging controller 120 includes a timing generator, a driver, and the like, and drives the imaging element 113 using the timing generator and the driver, thereby causing the imaging element 113 to convert, by photoelectric conversion, the reflected image of the affected area formed by the imaging optical system 111 to an electrical signal (an imaging signal for generating two-dimensional image data) every predetermined cycle, and causing the imaging signal to be output from the imaging element 113 to the image data generator 125. Note that the imaging signal includes at least a brightness signal and, typically, includes a brightness signal and a color difference signal.

The imaging controller 120 may further include functions for controlling the imager 110 so as to image a plurality of times at a substantially equal composition while varying exposure conditions; performing adjustment control of conditions such as auto focus (AF), auto exposure (AE), and auto white balance (AWB) when imaging a subject; and the like.

The image data generator 125 includes a function for generating, from the imaging signal that is an analog signal transferred from the imaging element 113, image data including at least one of converted dermoscopy image data Dt1, Dt2 and dermoscopy image data Dd that are digital signals. For example, after the image data generator 125 appropriately adjusts the gain for each RGB color component with respect to the imaging signal with analog value representation, the image data generator 125 samples and holds by a sample and hold circuit (not illustrated in the drawings) to convert the imaging signal to digital data using an analog/digital (A/D) converter (not illustrated in the drawings). Then, the image data generator 125 performs color processing including pixel interpolation processing and y correction processing using a color processing circuit (not illustrated in the drawings) and then generates, for each pixel, image data including a digital R value (value indicating the magnitude of the red component of that pixel), a digital G value (value indicating the magnitude of the green component of that pixel), and a digital B value (value indicating the magnitude of the blue component of that pixel). This image data is transferred to the storage 140 via a direct memory access (DMA) controller or the like (not illustrated in the drawings).

The storage 140 includes a function for storing (recording) the image data including at least one of the converted dermoscopy image data Dt1, Dt2 and the dermoscopy image data Dd processed by the image converter 160, the central controller 190, or the like, and outputting the image data to the image converter 160, the display 170, or the like on the basis of control of the central controller 190. The storage 140 is configured, for example, from read-only memory (ROM), random access memory (RAM), flash memory, and the like. The storage 140 may be implemented as a constituent that is provided fixed to a circuit board inside the diagnosis assistance device 1, may be implemented as a removable storage medium that is controlled by a storage medium controller (described later), or may be implemented as a combination thereof. Note that programs to be executed by a central processing unit (CPU) that is at least one of processors of the central controller 190, and data needed in advance to execute these programs are stored in the ROM. Data that is created or modified during the execution of the programs is stored in the RAM. Data that is to be retained even after the power of the diagnosis assistance device 1 is turned OFF is stored in non-volatile memory such as flash memory.

In one example, as illustrated in FIG. 3, a plurality of storage sections including a first storage section 141, a second storage section 142, and a third storage section 143 may be allocated in the storage 140. In this example, for example, the dermoscopy image data Dd imaged via the lesion imaging lens 200 is stored in the first storage section 141, the converted dermoscopy image data Dt1 capable of clarifying and revealing the affected area due to high dynamic range (HDR) conversion processing, obtained from the image converter 160, being performed is stored in the second storage section 142, and the converted dermoscopy image data Dt2 obtained by performing another image conversion processing by the image converter 160 is stored in the third storage section 143. Note that the image converter 160 can perform image conversion at any timing, and the image converter 160 can perform image conversion (for example, high dynamic range (HDR) conversion processing) using dermoscopy image data Dd that was imaged and stored in the storage 140 in the past instead of dermoscopy image data Dd that is presently imaged.

The storage medium controller includes a function for controlling the reading of data from and the writing of data to the storage medium that is removably attached to the diagnosis assistance device 1. Specifically, the storage medium controller encodes, in accordance with a predetermined encoding method (for example, JPEG format, motion JPEG format, MPEG format, or the like), the image data including at least one of the converted dermoscopy image data Dt1, Dt2 and the dermoscopy image data Dd, reads the image data from the storage medium, transfers the image data to the image converter 160, and the like. Note that, in this example, non-volatile memory (flash memory) or the like is implemented as the removable storage medium, but this is a non-limiting example, and can be modified as appropriate.

The image converter 160 includes a function for image converting the dermoscopy image data Dd to generate the converted dermoscopy image data Dt1, Dt2. Here, the converted dermoscopy image data Dt1 and Dt2 are converted dermoscopy image data that are created by different image conversion methods. There are various types of image conversion methods but, in one example, the converted dermoscopy image data Dt1 may be generated by an image conversion method by using a plurality of pieces of image data related to the dermoscopy image data Dd to perform high dynamic range (HDR) synthesis that widens the dynamic range. The converted dermoscopy image data Dt2 may be generated by an image conversion method in which a plurality of types of light sources having different peak wavelengths, for example, are used as the light sources 151 to combine a plurality of pieces of dermoscopy image data Dd imaged while switching the light sources 151 ON and OFF to make it easier to see symptoms in the affected area. Note that, here, an example is described in which two types of data, namely the converted dermoscopy image data Dt1, Dt2, are generated as the converted dermoscopy image data, but the image converter 160 may generate only one type of data, namely the converted dermoscopy image data Dt1. Additionally, the image converter 160 may generate three or more types of data, namely converted dermoscopy image data Dt1, Dt2, Dt3 . . . , using three or more types of image conversion methods.

In one example, the display 170 visually displays text, images, or the like on the basis of subject data and at least one of the converted dermoscopy image data Dt1, Dt2 and the dermoscopy image data Dd stored in the storage 140. The display 170 includes the display panel 171 and a display controller 172.

The display panel 171 is implemented as a liquid crystal display panel, an organic electro-luminescence (EL) display panel, or the like, and displays the image data and the like stored in the storage 140. The display controller 172 performs control to read and display, on the display panel 171, each piece of image data for displaying that is stored in the storage 140. Specifically, the display controller 172 may include video random access memory (VRAM), a VRAM controller, a digital video encoder, and the like. The digital video encoder reads the image data, decoded by the image converter 160 and stored in the VRAM, at a predetermined playback frame rate from the VRAM via the VRAM controller, generates a video signal on the basis of this data, and outputs the result to the display panel 171.

Note that, in FIG. 1, the display panel 171 is provided on the back surface side of the diagnosis assistance device 1, but the display panel 171 may be provided on the front surface side of the diagnosis assistance device 1. The display panel 171 may function as a touch panel by overlaying and providing a touch pad or the like. In this case, this touch panel also serves as the operation input device 180 by displaying an operation screen on the display panel 171. The display controller 172 may, for example, control the display panel 171 so as to display one image, or may control the display panel 171 so as to display a plurality of images side by side.

The operation input device 180 is an input interface that receives commands and the like from the user and outputs these commands to the central controller 190. The operation input device 180 includes a touch panel, a switch, a button, and the like. For example, the operation input device 180 includes the light type switching button 181 illustrated in FIG. 1 and the power button 182 illustrated in FIG. 2. In cases in which the display panel 171 is caused to function as a touch panel as described above, the operation input device 180 includes the display panel 171 (the touch panel). The operation input device 180 may also include operation buttons, switches, and the like that are provided separately from the light type switching button 181, the power button 182, the touch panel, and the like described above.

In one example, the operation input device 180 inputs target data including a target identification code into the diagnosis assistance device 1. The "target identification code" is a medical record number or the like, but the format thereof is not limited provided that it is a code that can identify a target such as a patient or a subject. Examples of the target identification code include a medical record number, a file number, an examination number, a name, a patient number, and the like. The target data may include the target identification code, basic information about the patient such as name, age, sex, address, and insurance number, main complaint, history of present illness, past medical history, family history, social history, preferences, existence of allergies, current symptoms/physical findings, appointment status, post-hospitalization developments/nursing records, treatment plans, and the like.

The central controller 190 controls the entire diagnosis assistance device 1. Specifically, the central controller 190 includes a CPU and the like, and performs various types of control operations according to various processing programs (not illustrated in the drawings) for the diagnosis assistance device 1. For example, by executing image analysis software stored in the storage 140, the central controller 190 can analyze the name of the medical condition (for example, whether a melanoma or the like) of the affected area in the captured image, analyze whether the affected area in the captured image is malignant, and the like. Additionally, by storing, in advance, an imaging control program, an image data generation program, an image conversion program, a display control program, and the like in the storage 140 and executing these programs using the CPU of the central controller 190, the CPU of the central controller 190 can be made to function as the imaging controller 120, the image data generator 125, the image converter 160, and the display controller 172 described above. In this case, in addition to the central controller 190, the imaging controller 120, the image data generator 125, the image converter 160, and the display controller 172 are also constituted by the CPU.

The central controller 190 may, in response to an input by the operation input device 180 of target data including the target identification code, associate one of the converted dermoscopy image data Dt1, Dt2 and the dermoscopy image data Dd with the target data that includes the target identification code such as a medical record number, and store the result in the storage 140. This is performed by writing the target data including the target identification code in a format such as Exif or the like to at least one of the converted dermoscopy image data Dt1, Dt2 and the dermoscopy image data Dd, and storing the result in the storage 140.

The diagnosis assistance device 1 includes a dermoscope lens 150 that is provided separately from the imager 110. The dermoscope lens 150 is for observing the affected area without imaging. The dermoscope lens 150 includes at least the observation lens 154 (optical lens) and the light sources 151 described above, and enables the visual observation of the affected area through the observation lens 154. Thus, the diagnosis assistance device 1 can include both a dermoscope (loupe) function that uses the dermoscope lens 150 and a dermoscope imaging function that uses the imager 110. Therefore, it is possible to continuously carry out, by a single device, procedures conventionally performed using a plurality of devices. Specifically, it is possible to continuously carry out, by a single device, (1) screening for whether the affected area is a benign pigmented nevus or a malignant melanoma by a dermoscope (loupe), and (2) magnified imaging of the affected area by dermoscopy imaging.

The observation lens 154 of the dermoscope lens 150 is a magnifying lens that magnifies the affected area, and functions as a magnifying glass, that is, a so-called loupe, that is looked through from the back surface side to observe the affected area. The magnification power of the observation lens 154 is, for example, from 5-times to 30-times. The observation lens 154 may be implemented as any of a one double-sided convex lens, a lens in which two or a plurality of convex lenses are combined, one achromat lens, and a lens in which two or more achromat lenses are combined. Additionally, the observation lens 154 may be implemented as an aberration lens. Furthermore, the observation lens 154 may be obtained by incorporating an aspherical lens into a spherical lens to obtain excellent optical properties and reduce distortion. The observation lens 154 may further include an antireflection film, a color filter, or the like. In one example the lens diameter of the observation lens 154 is set to 15 mm.

One or a plurality of the light sources 151 are arranged on the outer periphery of the observation lens 154. The light sources 151 are turned on as necessary and are used to illuminate the subject. As illustrated in FIG. 2, the light sources 151 are arranged at equal intervals on an annular line slightly larger than the outer periphery of the observation lens 154. While not illustrated in the drawings, the light sources 151 may be arranged so that optical axes thereof are inclined with respect to a center axis of the observation lens 154, so that the light emitted from the light sources 151 concentrates in a center direction of the observation lens 154. Examples of the light sources 151 include high-brightness lights such as halogen lamps, light-emitting diodes, and light-emitting devices such as semiconductor light-emitting devices and organic electro-luminescence devices.

When a plurality of the light sources 151 is provided, the plurality of light sources 151 may include light sources of the same wavelength, or may include light sources of mutually different wavelengths. For example, ultraviolet or blue light is easily absorbed by pigmentation areas and, as such, can be used to suitably visualize pigmentation areas. Likewise, green light is easily absorbed by blood vessels and, as such, can be used to suitably visualize blood vessels. White light can be used to obtain anatomical information used in the observation of skin disorders, or can be used to suitably visualize the skin surface.

Accordingly, the plurality of light sources 151 may be configured such that, when a light source 151 of one wavelength is ON, the light sources 151 of wavelengths different from the one wavelength are OFF, or when the light sources 151 of the other wavelengths are ON, the light source 151 of the one wavelength is OFF. Due to this configuration, a plurality of pieces of dermoscopy image data Dd can be obtained by imaging while switching the light sources 151 of various wavelengths ON and OFF, and information about the interior of the skin can be more suitably obtained. Moreover, examination, observation, and treatment of the target area can be facilitated by comparing and/or superimposing the plurality of pieces of dermoscopy image data Dd.

Note that the light sources 151 may further include a focus lens for focusing the light. Additionally, the light sources 151 are electrically connected to a wiring of a circuit board inside the diagnosis assistance device 1. This wiring is electrically connected to a battery, external power supply, or other power supply. When the light type switching button 181 (the operation input device 180) illustrated in FIG. 1 is pressed, the central controller 190 controls the dermoscope lens 150 to change the type (halogen lamp, light emitting diode, organic electroluminescence, and the like), wavelength, brightness, and the like of the light used by the light sources 151.

Next, the microphone 401, the sound recorder 400, and the time keeper 500 illustrated in FIG. 3 are described. The diagnosis assistance device 1 includes the microphone 401 that collects voice, the sound recorder 400 that records voice data Dv collected by the microphone 401, and the time keeper 500 that measures time and acquires time data Dh.

The microphone 401 has a function of collecting sound that includes voice. In FIG. 1, an example is illustrated in which the microphone 401 is implemented as a monaural microphone disposed on the back surface of the diagnosis assistance device 1, but the aspect of the microphone 401 is not limited thereto. The microphone 401 may be implemented as a stereo microphone or a zoom microphone, or may be implemented as a wired or wireless external microphone 401 instead of being built-into the diagnosis assistance device 1.

The sound recorder 400 records the voice data Dv at the examination site that is collected by the microphone 401 during the examination of the affected area. Regarding the recording of the voice data Dv, the sound recorder 400 may include memory for recording the voice data Dv, or may record the voice data Dv in the storage 140.

The time keeper 500 is a module that measures time and acquires the time data Dh. The time keeper 500 can measure a current time by measuring an elapsed time from a preset time. Additionally, the time keeper 500 can output the current time (date and time) as a time stamp. For example, when the imager 110, the sound recorder 400, and the like are to operate, the central controller 190 can acquire start/end times (dates and times) thereof from the time keeper 500, and append the start/end times to the captured image, the voice data Dv, or the like as time stamps. Due to this configuration, examination facts and details can be defined from both perspectives of the captured image and the voice data Dv, can be used at a later time or later date as reference material when filling out a medical record, and can be used as evidence in the event that trouble of some sort with the patient occurs.

The central controller 190 starts up the sound recorder 400 by a predetermined trigger (determination that a recording condition (described later) is met), appends, as a time stamp, the time data Dh acquired by the time keeper 500 to the voice data Dv recorded by the sound recorder 400, and stores the resultant voice data Dv in the storage 140. As a result, the physician can confirm the examination process after the end of the examination, and the stored voice data Dv can be of benefit to creating an electronic medical record. Furthermore, at successive times of examinations, the physician can confirm, with the patient, changes in the medical condition, thereby contributing to informed consent.

In addition to the physician and/or the patient, the sound recorder 400 can record the voice data Dv of nurses, family of the patient, and the like as data of voice at the examination site. Note that the time keeper 500 typically performs time keeping operations. In the following description, it is mentioned that the sound recorder 400 and the time keeper 500 are started up by a predetermined trigger, but this should be understood to mean that the time keeper 500 determines, by a predetermined trigger, the start time at which the sound recorder 400 starts recording.

In one example, the predetermined trigger for the central controller 190 storing the voice data Dv in the storage 140 is when it is detected that a patient is being examined by the dermoscope lens 150. Specifically, based on the settings of the predetermined trigger, the central controller 190 records the voice data Dv during examinations and does not record the voice data Dv when an examination is not being carried out. The sound recorder 400 can acquire the voice (the voice data Dv) at the examination site by, for example, recording the examination process and results of the medical condition in real time and as sound, recording conversations and the like between the physician, nurse, patient, and/or family of the patient, and the like.

The predetermined trigger for starting up the sound recorder 400 and the time keeper 500 can be configured by various aspects. For example, the detection, by the central controller 190, of the physician manually turning a dedicated switch (record button) ON or OFF, or the detection of the power button 182 of the diagnosis assistance device 1 being turned ON or OFF may be set as the trigger for the central controller 190 to turn the sound recorder 400 and the time keeper 500 ON or OFF. Furthermore, the central controller 190 may handle an ON state of the light sources 151 of the diagnosis assistance device 1 as an examination being carried out, for use as the trigger for starting up the sound recorder 400 and the time keeper 500.

Furthermore, when imaging by the imager 110 of the diagnosis assistance device 1, at the start of operation of the diagnosis assistance device 1 by the physician, the physician may input the target identification code such as a medical record number via the touch panel (the display panel 171) and press an OK button to start associated imaging, and touch an END button to end the associated imaging, and the sound recorder 400 may turn the recording ON and OFF in conjunction with the start and end of the associated imaging. Due to the configuration described above, the voice data Dv during examination can be efficiently stored in the storage 140. Note that, it is possible to configure more thoroughly such that, while the sound recorder 400 is ON, recording is carried out only when voice from the physician, nurse, patient, and/or family of the patient is picked up.

The central controller 190 may execute image analysis software that analyzes captured images, and use the results of the image analysis as a trigger. For example, a case in which a captured image is analyzed by the image analysis software and determination is made that the affected area is a melanoma may be used as the trigger. Alternatively, a case in which a captured image is analyzed by the image analysis software and determination as to whether the affected area is malignant is made that the affected area may be malignant may be used as the trigger. Note that, in either case, the central controller 190 performs the determination by executing the image analysis software.

In one example, the central controller 190 acquires a plurality of pieces of image data including position information of the diseased area (affected area) and a diffuse reflectance spectrum at that position, regards the diffuse reflectance spectrum as a multidimensional vector, calculates an angle formed by this multidimensional vector and a reference vector, obtains, on the basis of the angle and the position information of the image data, condition data Dc that reflects the molecular information on the surface of the affected area related to the medical condition, and uses this condition data Dc and a predetermined threshold to determine whether the affected area is a melanoma and whether the affected area is malignant or benign. Note that technology for identifying lesions by machine learning are advancing and, as such, the central controller 190 may be configured to identify whether the affected area is a melanoma or whether the affected area is malignant or benign by image identification processing using machine learning.

The voice data Dv recorded by the sound recorder 400 can be played back at any time. For example, the physician can, when necessary, call up and play back the dermoscopy image data Dd, the converted dermoscopy image data Dt1, or the converted dermoscopy image data Dt2 stored in the storage 140 of the diagnosis assistance device 1. Additionally, the physician may simultaneously playback the voice data Dv from when that image data was captured by using, in conjunction with the playback of the images, the time stamps appended to the image data and the voice data Dv.

In addition to the various constituents described above, the diagnosis assistance device 1 may also include a position detector. The position detector has a function for detecting the position of the position detector. For example, the position detector can, on the basis of a signal output from a GPS satellite or the like, generate position information indicating the current position of the diagnosis assistance device 1. Such a configuration makes it possible for a physician to define the location (hospital, clinic, recreation facility, home, or the like) where the patient was examined, at the same time of the time stamp.

Next, a use method and a control method of the diagnosis assistance device 1 according to the present embodiment are described. When the power button 182 of the diagnosis assistance device 1 is turned ON, a function selection menu is displayed on the display panel 171. The function selection menu is a menu in which the various functions of the diagnosis assistance device 1 (associated imaging function, image list display function, and the like) are displayed as buttons on a screen. The user touches the buttons of the various functions to start up specific functions of the diagnosis assistance device 1.

First, the associated imaging function of the functions of the diagnosis assistance device 1 is described. This is a feature for associating a series of captured images.

First, a case is described in which, when capturing a plurality of photographs of one patient, a series of images are associated on the basis of a medical record number or the like. When the power of the diagnosis assistance device 1 is turned ON, the function selection menu is displayed on the display panel 171 (the touch panel). When the user touches the "associated imaging function" of the functions listed in the function selection menu (on the operation input device 180), "associated imaging", which is a function for associating a series of image data of the affected area to be imaged, is started. Moreover, a screen for inputting the target identification code such as a medical record number is displayed on the display panel 171 (the touch panel). When the user inputs, on the touch panel (the operation input device 180), the target identification code of the patient to be imaged, an operation menu such as, for example, "Lesion Imaging", "Imaging End", or the like is displayed on the display panel 171, and the diagnosis assistance device 1 enters an imaging stand-by state.

When, in the imaging stand-by state, the user touches the "Lesion Imaging" button in the operation menu, the diagnosis assistance device 1 dermoscopically images the affected area using the imager 110, and stores the dermoscopically obtained image data in the storage 140 as the dermoscopy image data Dd. At this time, information such as the target identification code is written in a format such as Exif to the dermoscopy image data Dd, and the result is stored in the storage 140. When imaging the affected area, the central controller 190 may be controlled so as to associate at least two of the dermoscopy image data Dd and the converted dermoscopy image data Dt1, Dt2, and store the result in the storage 140. In this case, the central controller 190 stores the at least two of the dermoscopy image data Dd and the converted dermoscopy image data Dt1, Dt2 as one data set (record) in the storage 140.

Conventionally, when capturing at least one of a normal image in which the affected area is captured by a typical digital camera and a dermoscopy image in which the affected area is magnified using a special magnification lens and captured so that a dermatologist or the like can ascertain the general position (for example, "left wrist" or the like) of the diseased area (affected area), target data capable of identifying the target, such as the medical record of the patient, is imaged in order to identify the target after these images are captured. This is to identify the target on the basis of the captured target data and manually organize the images. However, the amount of image data is enormous and organizing images is complicated and requires a great deal of effort.

In contrast, with the present embodiment, at least one of the converted dermoscopy image data Dt1, Dt2 and the dermoscopy image data Dd are associated and stored in the storage 140. As such, the labor of organizing the images is eliminated and the target information such as the patient can be accurately organized in a short amount of time. Additionally, there are cases in which images are shown to the patient using the display 170 but, by enabling searching using the target data, the risk of inadvertently showing images of other targets stored in the diagnosis assistance device 1 can be avoided.

After the imaging, the diagnosis assistance device 1 returns to the imaging stand-by state. When the user touches "Imaging End" in the menu while in the imaging stand-by state, the associated imaging function is ended. When the associated imaging function is ended, the image list display function is started up and a list of associated images (image data of the patient represented by the target identification code) including at least one of the converted dermoscopy image data Dt1 and the converted dermoscopy image data Dt2, and the dermoscopy image data Dd is displayed on the display 170. Note that the diagnosis assistance device 1 may be configured to return to the screen on which the function selection menu is displayed when the associated imaging function is ended.

As described above, in each piece of the image data, voice data Dv recorded by the sound recorder 400 and time data Dh time stamped by the time keeper 500 (when the position detector is provided, also the position information detected by the position detector) are stored in association with each image on a one-to-one basis for each of target identification code. The data structure at this time consists of, for example, a physician identification (ID), a patient ID, an image ID, the voice data Dv, the time data Dh, and the condition data Dc, and these are stored together with the image data as a set in the storage 140. As with the target identification code, these pieces of data (the various IDs, the time data Dh, the condition data Dc, and the like) may be stored in the storage 140 by writing these pieces of data to the image data in a format such as Exif or the like.

Here, the physician ID is an identifier for uniquely identifying the physician, the patient ID is an identifier for uniquely identifying the patient, and the image ID is an identifier for uniquely identifying the image. When using this data structure, the central controller 190 of the diagnosis assistance device 1 executes processing for acquiring the physician ID, processing for acquiring the patient ID, processing for acquiring the image ID, processing for starting up at a predetermined trigger and recording the time data Dh and the voice data Dv in the storage 140, processing for acquiring the condition data Dc based on the examination results obtained from the captured image acquired by the imager 110 of the diagnosis assistance device 1, and processing for associating and storing each of the physician ID, the patient ID, the voice data Dv, the time data Dh, and the condition data Dc in the storage 140.

In correspondence with these processings, the CPU of the diagnosis assistance device 1 may further include a function of acquiring the physician ID of the physician that uses the diagnosis assistance device 1, a function of acquiring the patient ID of the patient that is the subject, and a function of acquiring the condition data Dc based on the examination results. In this aspect, the CPU of the central controller 190 associates the physician ID, the patient ID, and the condition data Dc with the voice data Dv and stores the result in the storage 140. Various aspects can be used for the function of acquiring the physician ID and the function of acquiring the patient ID of the patient. For example, the central controller 190 may acquire the various IDs by key inputs or the like using the operation input device 180. Additionally, a barcode of an identification card, a fingerprint, a face, or the like may be imaged by the imager 110, the central controller 190 may perform image recognition thereon, and the IDs may be acquired by barcode recognition, fingerprint recognition, facial recognition, or the like. Moreover, the central controller 190 may be connected to a magnetic reading device and acquire the IDs by reading the magnetism of the identification card using the magnetic reading device.

For the condition data Dc, from the perspective of efficiently and accurately carrying out examinations, it is preferable that a list of candidates which, based on the image analysis software, have a high possibility of being the medical condition of the affected area, is displayed on the display 170, and a function of acquiring the condition data Dc are provided by the CPU so that the condition data Dc is acquired by selecting from the list.

Next, the image list display function that starts up when "Image List Display" is touched from the function selection menu is described. The image list display function is a function for displaying only images of a specific patient (only images associated with the target identification code that is input) from among the image data stored in the storage 140.

When the user turns the power of the diagnosis assistance device 1 ON, the function selection menu is displayed on the display panel 171 (the touch panel). Then, when the user selects "Image List Display" from the function selection menu, the image list display function starts up and a screen for inputting the target identification code such as a medical record number or the like is displayed on the display panel 171 (the touch panel). Then, when the user inputs, on the touch panel, the target identification code (medical record number or the like) of the patient to be displayed, a list of thumbnails of images consisting only of images of image data associated with that target identification code is displayed on the display panel 171. Note that, as described above, in the present embodiment, in order to improve convenience, when the associated imaging function is ended as well, the image list display function starts up and a list of thumbnails of images, consisting only of images of image data associated with the target identification code input when the associated imaging function is started up, is displayed on the display panel 171.

In this case, when the thumbnails of the various images are tapped, the selected images are displayed on the display panel 171. Here, for example, a dermoscopy image can be displayed, a converted dermoscopy 1 image can be displayed, a converted dermoscopy 2 image can be displayed, or the like. These images that are displayed on the display panel 171 can be switched by a swipe operation on the display panel 171 that is a touch panel, or by other input operations of the operation input device 180.

These images consist only of images of the image data that is associated with the target identification code, and images of other patients are not displayed on the display panel 171. As such, the risk of inadvertently showing images of other patients that are stored in the diagnosis assistance device 1 when explaining current and past examination states to a specific patient can be avoided.

As described above, after the examination, the central controller 190 may display, as the condition data Dc, a candidate list for the condition data Dc on the display panel 171. For example, the central controller 190 may display, as the candidate list, typical skin lesions such as "basal cell carcinoma", "seborrheic keratoses", and "pigmented nevus" in addition to the distinction between "benignancy" and "malignance."

The image analysis software analyzes the image data, selects, from the list, a disease name that is highly likely to be the name of the medical condition of the affected area, and acquires, as the condition data Dc, the disease name that corresponds to the examination results. At this time, in order to facilitate confirmation by the doctor, the nurse, or the like, the central controller 190 may configure the display panel 171 to highlight the display of the likely disease name by changing the color of the disease name or causing the disease name to flash, or may display, on the display panel 171, images of cases stored in advance for each disease name. In the example described above, it is described that four typical disease names are displayed as the condition data Dc, but this is merely an example. For example, a configuration is possible in which, for example, about 20 cases are stored in the storage 140, the image analysis software is used to search for cases similar to the examination results, and some cases with high similarity are displayed on the display panel 171.

The associated imaging function and the image list display function carried out by the diagnosis assistance device 1 are described above. Next, sound storing processing performed by the diagnosis assistance device 1 is described while referencing FIG. 4. The sound storing processing is processing for the central controller 190 to automatically perform voice recording by the sound recorder 400. This processing starts when the power of the diagnosis assistance device 1 is turned ON.

Figure 4:
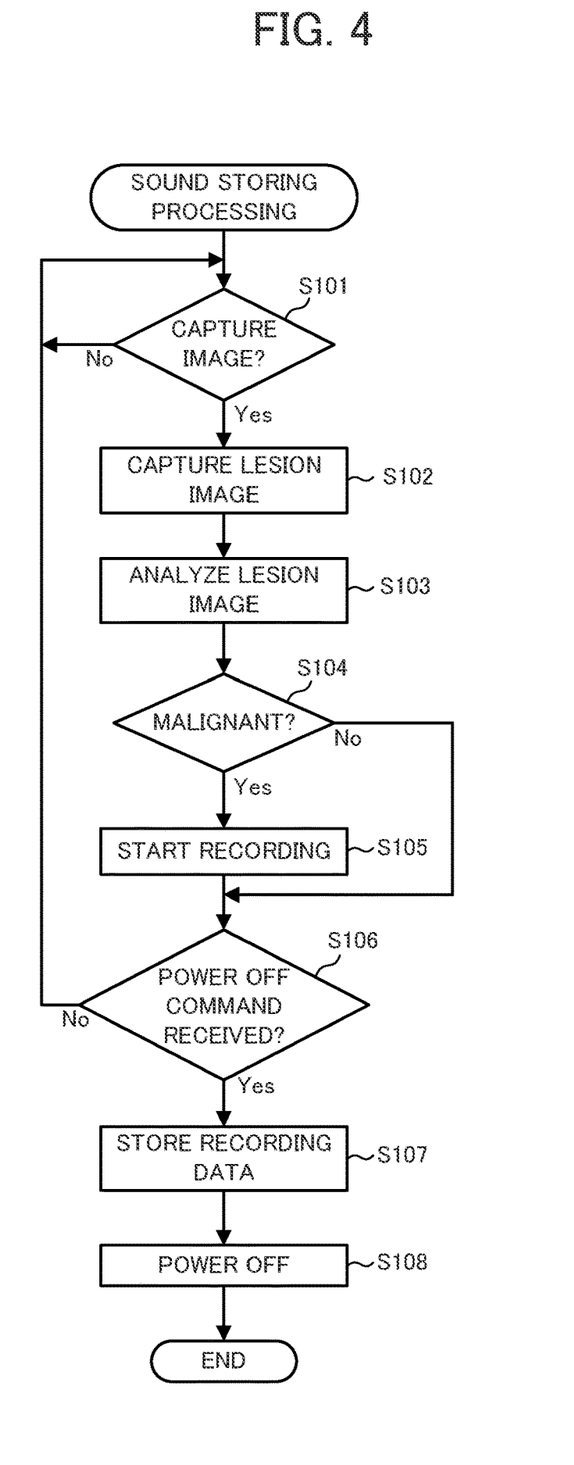
FIG. 4 is a flowchart of sound storing processing according to Embodiment 1.

First, the central controller 190 determines whether a command for imaging is received by the operation input device 180 (step S101). In one example, a command for imaging is determined to be received when the user touches "Lesion Imaging" in the operation menu.

If a command for imaging is not received (step S101; No), step S101 is executed. If a command for imaging is received (step S101; Yes), the central controller 190 captures a lesion image using the imager 110 (step S102).

Then, the central controller 190 uses the image analysis software to analyze the lesion image (step S103), and determines whether the affected area in the lesion image is malignant (step S104). In the present embodiment, the recording condition is determined to be met when determination is made that the affected area is malignant.

When determination is made that the affected area is not malignant (step S104; No), step S106 is executed. When determination is made that the affected area is malignant (step S104; Yes), the central controller 190 starts recording by the sound recorder 400 (step S105).

Then, the central controller 190 determines whether a command for turning the power OFF is received by the operation input device 180 (step S106). For example, a command for turning the power OFF is determined to be received when the user sets the power button 182 to OFF.

If a command for turning the power OFF is not received (step S106; No), step S101 is executed. If a command for turning the power OFF is received (step S106; Yes), the central controller 190 stores, in the storage 140, the recording data recorded by the sound recorder 400 (step S107). Note that, as described above, a time stamp acquired by the time keeper 500 is appended to this recording data and, as such, a time stamp is stored together with the recording data in the storage 140. Then, the central controller 190 turns the power of the diagnosis assistance device 1 OFF (step S108), and ends the sound storing processing.

The diagnosis assistance device 1 according to Embodiment 1 executes the sound storing processing described above, thereby storing, in the storage 140, recording data of cases in which determination is made that the affected area is malignant. As such, there is an advantageous effect of storing only important conversations between the physician and the patient, and unnecessary recording data is not stored.

Embodiment 2

The configuration of a diagnosis assistance device 2 according to Embodiment 2 is the same as that of the diagnosis assistance device 1. However, the processing content of sound storing processing executed by the central controller 190 is somewhat different. The sound storing processing according to Embodiment 2 is described while referencing FIG. 5. When the power of the diagnosis assistance device 2 is turned ON, the sound storing processing illustrated in FIG. 5 starts.

Figure 5:
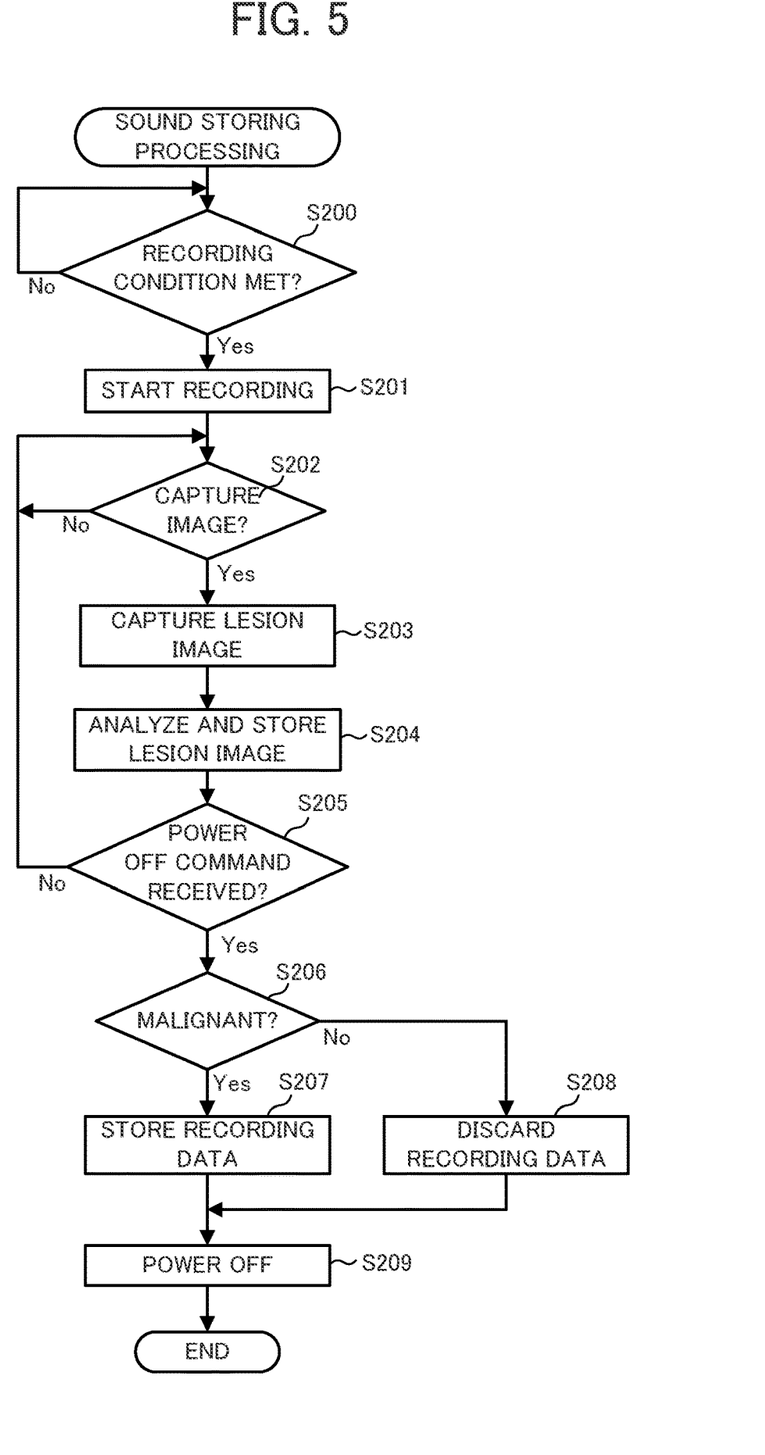
FIG. 5 is a flowchart of sound storing processing according to Embodiment 2.

First, the central controller 190 determines whether a recording condition is met (step S200). The recording condition is a condition for starting recording using the sound recorder 400. In this case, the recording condition is determined to be met when the power of the diagnosis assistance device 2 is turned ON.

If the recording condition is not met (step S200; No), step S200 is executed. If the recording condition is met (step S200; Yes), the central controller 190 starts the recording using the sound recorder 400 (step S201). Specifically, when the power of the diagnosis assistance device 2 is turned ON due to the start of an examination, recording of the voice during the examination is started. Next, the central controller 190 determines whether a command for imaging is received by the operation input device 180 (step S202).

If a command for imaging is not received (step S202; No), step S202 is executed. If a command for imaging is received (step S202; Yes), the central controller 190 captures a lesion image using the imager 110 (step S203).

Then, the central controller 190 uses the image analysis software to analyze the lesion image, and stores the analysis results in the storage 140 (step S204).

Then, the central controller 190 determines whether a command for turning the power OFF is received by the operation input device 180 (step S205). If a command for turning the power OFF is not received (step S205; No), step S202 is executed.

When a command for turning the power OFF is received (step S205; Yes), determination is made whether there is, among the analysis results saved in step S204, even one affected area in the lesion image that is analyzed as being malignant (step S206).

If, among the analysis results, there is not even one affected area in the lesion image that is analyzed as being malignant (step S206; No), the central controller 190 discards the recording data recorded by the sound recorder 400 (step S208) and executes step S209. If, among the analysis results, there is even one affected area in the lesion image that is analyzed as being malignant (step S206; Yes), the central controller 190 stores, in the storage 140, the recording data recorded by the sound recorder 400 (step S207). Note that, as described above, a time stamp acquired by the time keeper 500 is appended to this recording data and, as such, a time stamp is stored together with the recording data in the storage 140.

Then, the central controller 190 turns the power of the diagnosis assistance device 2 OFF (step S209), and ends the sound storing processing. Note that, in step S200, it is described that the recording condition is determined to be met when the power of the diagnosis assistance device 2 is turned ON, but this is merely an example. For example, the central controller 190 may determine that the recording condition is met when it is detected that the light type switching button 181 is pressed. In this case, the central controller 190 turns the light sources 151 ON due to the detection of the light type switching button 181 being pressed and, as such, voice is recorded from the time at which the light sources 151 are turned ON. Additionally, the CPU of the central controller 190 may include a voice recognition function, and the recording condition may be determined to be met when voice such as "Mr./Ms. XXX (name of patient), please come in" is recognized.

The diagnosis assistance device 2 according to Embodiment 2 executes the sound storing processing described above, thereby discarding the recording data in cases in which determination is made that the affected area is not malignant (that is, cases in which determination is made the affected area is benign). As such, there is an advantageous effect of not storing unnecessary recording data. Additionally, since conversations after the recording condition is met are constantly recorded, there is an advantageous effect in that, when determination is made that an affected area is malignant, all of the conversations between the physician and the patient, including those both before and after the examination, can be stored.

Embodiment 3

The configuration of a diagnosis assistance device 3 according to Embodiment 3 is the same as that of the diagnosis assistance device 1. However, the processing content of sound storing processing executed by the central controller 190 is somewhat different. The sound storing processing according to Embodiment 3 is described while referencing FIG. 6. When the power of the diagnosis assistance device 3 is turned ON, the sound storing processing illustrated in FIG. 6 starts.

Figure 6:
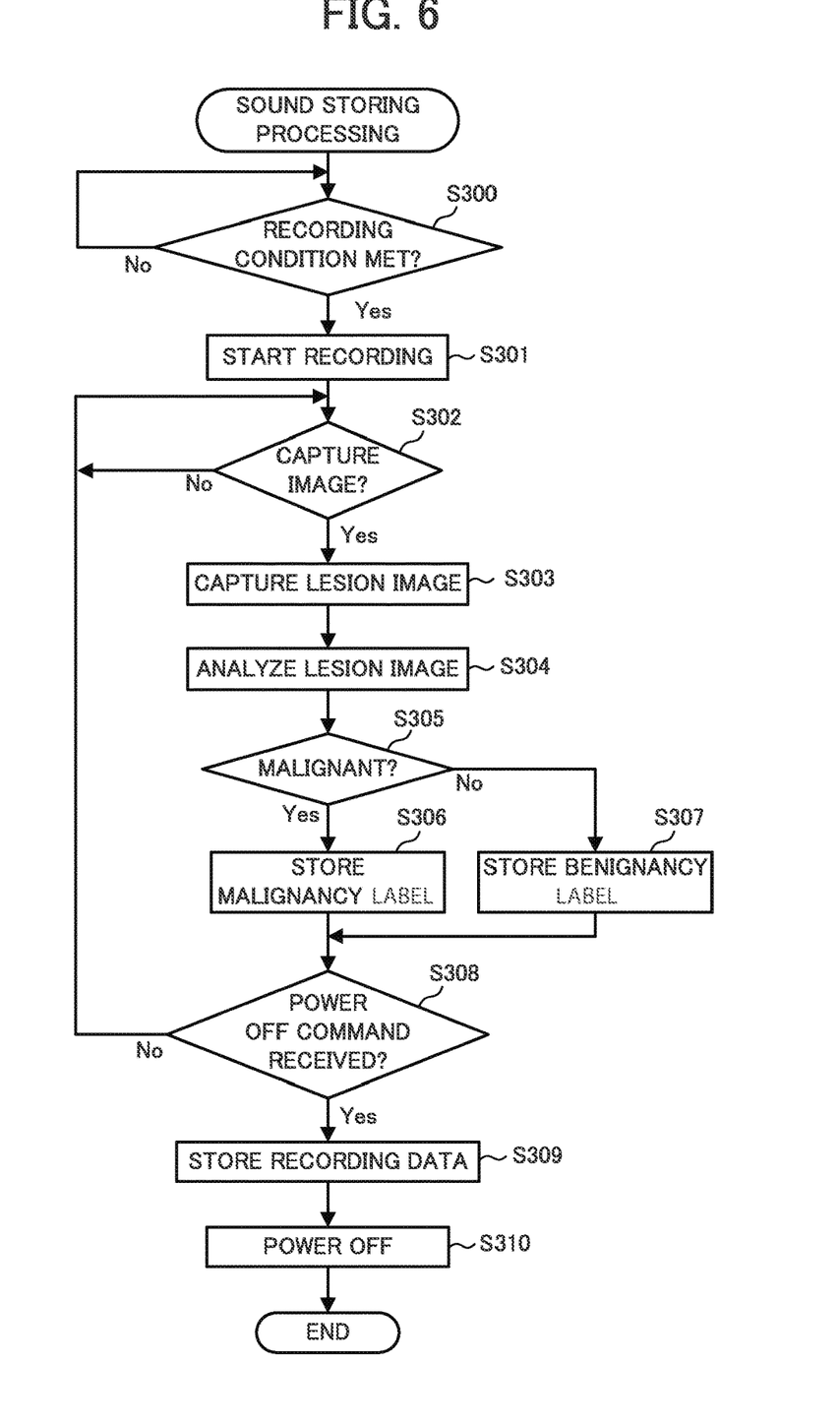
FIG. 6 is a flowchart of sound storing processing according to Embodiment 3.

In the sound storing processing, steps S300 to S303 are the same as steps S200 to S203, respectively, of the sound storing processing according to Embodiment 2 and, as such, description thereof is forgone.

When the processing of step S303 ends, the central controller 190 uses the image analysis software to analyze the lesion image (step S304). Then, the central controller 190 determines whether the affected area in the lesion image analyzed in step S304 is malignant (step S305).

If it is analyzed that the affected area in the lesion image is malignant (step S305; Yes), the central controller 190 stores, in the storage 140, a malignancy label obtained from the analysis results together with a time stamp acquired from the time keeper 500 (step S306) and executes step S308. The malignancy label obtained from the analysis results is a label that expresses a type of malignancy of the affected area and, for example is the name of a malignant medical condition (malignant melanoma, basal cell carcinoma, or the like).

Meanwhile, if it is analyzed that the affected area in the lesion image is not malignant (step S305; No), the central controller 190 stores, in the storage 140, a benignancy label obtained from the analysis results together with a time stamp acquired from the time keeper 500 (step S307) and executes step S308. The benignancy label obtained from the analysis results is a label that expresses a type of benignancy of the affected area and, for example is the name of a benign medical condition (pigment cell nevus, seborrheic keratosis, or the like).

Then, in step S308, the central controller 190 determines whether a command for turning the power OFF is received by the operation input device 180. If a command for turning the power OFF is not received (step S308; No), step S302 is executed.

If a command for turning the power OFF is received (step S308; Yes), the central controller 190 embeds, in the recording data recorded by the sound recorder 400, the labels saved in the steps S306 and S307 (the benignancy label and the malignancy label), and stores the result in the storage 140 (step S309). When embedding the labels in the voice data, the central controller 190 embeds, on the basis of the information of the time stamps stored with the labels, the labels in the position of the corresponding time of the voice data.

Then, the central controller 190 turns the power of the diagnosis assistance device 3 OFF (step S310), and ends the sound storing processing.

Note that, in step S309, of the recording data recorded by the sound recorder 400, the central controller 190 may store, in the storage 140 and together with the malignancy label, only the portion corresponding to the malignancy label stored in step S306 and dispose of the portion corresponding to the benignancy label stored in step S307 without storing this portion in the storage 140.

In the sound storing processing described above, the central controller 190 starts the recording in step S301 but, as with the sound storing processing according to Embodiment 1, the central controller 190 may start the recording in step S306 (if it is analyzed that the affected area in the lesion image is malignant in step S304) instead of starting the recording in step S301.

The diagnosis assistance device 3 according to Embodiment 3 executes the sound storing processing described above, thereby constantly recording conversations after the recording condition is met. As such, there is an advantageous effect in that all of the conversations between the physician and the patient, including those both before and after the examination, can be stored. Additionally, since the analysis results of the lesion image are embedded in the voice data as labels, there is an advantageous effect in that, when there is a medical condition that is of concern to the physician, the voice data can be searched using the label corresponding to that medical condition, and the voice data can be efficiently confirmed.

Examination System

As described above, the diagnosis assistance devices 1, 2, and 3 can be configured as examination systems by being connected to an external computer. In such a case, the diagnosis assistance devices 1, 2, or 3 further includes a communicator that sends and receives information such as image data to and from an external device (computer) such as a personal computer. Moreover, in this examination system, the diagnosis assistance device 1, 2, or 3 may have a configuration in which a portion or all of the storage 140, the display 170, and the operation input device 180 is provided on the external device side. In such a case, for example, a storage medium (removable storage medium, storage medium of the external device, or the like) outside the diagnosis assistance device 1, 2, or 3 can be used as the storage 140. Additionally, a display device or the like of the external device can be used as the display 170. Moreover, a keyboard, a pointing device such as a mouse, a voice recognition device, or the like of the external device can be used as the operation input device 180.

More specifically, an examination system for examining medical conditions includes the diagnosis assistance device 1 that images a subject, and an external device (computer) connected to the diagnosis assistance device 1. The diagnosis assistance device 1, 2, or 3 includes the imager 110 that images the subject to acquire a captured image, the sound recorder 400 that records the voice data Dv at the examination site using the microphone 401, the time keeper 500 that measures time to acquire the time data Dh, the storage 140 that stores the results of the examination, and the central controller 190 that controls the diagnosis assistance device 1, the sound recorder 400, the time keeper 500, and the storage 140.

The central controller 190 starts up the sound recorder 400 by a predetermined trigger, appends, as a time stamp, the time data Dh acquired by the time keeper 500 to the voice data Dv recorded by the sound recorder 400, and transfers the result to the external device. The central controller 190 transfers captured images acquired by the imager 110 to the external device. The external device manages the captured images using image management software.

The image management software may automatically create an electronic medical record of the patient by converting the voice data Dv to text, and combining the text with the physician ID, the patient ID, and the image ID that are separately input as illustrated in the data structure described above. As a result, the labor of filling in paper medical records during and after examinations can be eliminated, and examinations can be efficiently carried out.

Here, in cases in which an electronic medical record is created, when the examination results are to be provided as, for example, medical data to a third party, or when a third party attempts to access the electronic medical record without authorization, it is critical to prevent the patient from being identified on the basis of the image ID and the patient ID and to prevent the disclosure of the personal information of the patient to the third party. As such, in the present embodiment, information leakage prevention measures for electronic medical records are implemented. For example, identity verification of a photographer (the physician or the like) of the subject, setting of a secret key corresponding to the photographer and the patient, creation of image information in which personal information is removed from medical image information, encryption of the information attached to the medical images, management of third-party institutions, and the like are configured as subsystems of the examination system.

Note that, in this examination system, the voice data Dv, the time data Dh, and the condition data Dc described above, and the like, may be individually sent to the external device by the central controller 190, and may be associated by the image management software in the external device. Furthermore, the storage 140 may be implemented in the external device.

The external device may include image analysis software for analyzing captured images, and the external device may analyze the images instead of the central controller 190. In this case, for example, the image analysis software may analyze the captured image and determine whether the medical condition (the subject during examination) is a melanoma, and cases in which determination is made that the medical condition is a melanoma may be set as the predetermined trigger for starting up the sound recorder 400 and the time keeper 500. Alternatively, the image analysis software may analyze the captured image and determine whether the medical condition (the subject during examination) is malignant, and cases in which determination is made that the medical condition is malignant may be set as the predetermined trigger.

The determination method of the image in this case is the same as that of the determination method by the central controller 190 described above. As with the central controller 190, the external device may also be configured to identify whether the affected area is a melanoma or whether the affected area is malignant or benign by image identification processing using machine learning.

In the embodiments described above, the central controller 190 carries out processing in which recording by the sound recorder 400 is continued from after determination is made that the recording condition is met until there is a command to turn the power OFF. However, this processing is merely an example. For example, the central controller 190 may stop the recording by the sound recorder 400 on the basis of the detection of the light sources 151 being turned OFF, the recording button being set to OFF, or the like. Due to such a configuration, it is possible to record, by the sound recorder 400, voice only while the recording condition is met.

In the embodiments described above, the diagnosis assistance device 1, 2, or 3 includes the imaging element 113, the observation lens 154, and the microphone 401 in the same housing as the diagnosis assistance device 1, 2, or 3, but some or all of these constituents may be provided as separate bodies.

Advantageous Effects of the Embodiments

The embodiments described above demonstrate advantageous effects such as enabling the preservation, as records, of important conversations had during examinations, the use of such records when studying the medical conditions post-examination, and the preservation of conversations as evidence. Additionally, a liquid crystal display is attached to the dermoscope, the lesion image is selected from a condition data candidate list and/or time stamps, and examination notes can be easily recorded by voice. As such, the embodiments described above demonstrate advantageous effects such as the date and time at which the lesion of concern is observed can be recorded, disease name candidates can be preserved as records, and such data can be used as reference material when studying the medical conditions post-examination.

The various functions of the diagnosis assistance device 1, 2, or 3 can be implemented by a computer such as a typical personal computer (PC). Specifically, in the embodiments described above, examples are described in which various software and the program of the sound storing processing performed by the diagnosis assistance device 1, 2, or 3 are stored in advance in the ROM of the storage 140. However, a computer may be configured that is capable of realizing these various features by storing and distributing the programs on a non-transitory computer-readable recording medium such as a compact disc read-only memory (CD-ROM), a digital versatile disc (DVD), a magneto-optical disc (MO), a memory card, and universal serial bus (USB) memory, and reading out and installing these programs on the computer.

Preferred embodiments of the present disclosure have been described, but the present disclosure should not be construed as being limited to these specific embodiments. The scope of the invention is defined only by the included claims, along with the full range of equivalents to which such claims are entitled.

The invention claimed is:

1. A diagnosis assistance device comprising:
   at least one microphone capable of collecting voice around an affected area; and
   at least one processor configured to
   execute image analysis software to determine, based on image data that is data of a captured image of the affected area, whether the affected area is malignant, and
   determine whether a recording condition is met,
   execute recording control for controlling so that recording of the voice collected by the at least one microphone is started with the recording condition being met,
   when a determination is made by the image analysis software that the affected area is malignant, store in a memory the voice collected by the at least one microphone and recorded by executing the recording control when the recording condition is met, the determination that the affected area is malignant serving as a trigger that causes the at least one processor to store the voice recorded by executing the recording control in the memory, and
   when a determination is made by the image analysis software that the affected area is not malignant, discard the voice recorded by executing the recording control when the recording condition is met, the determination that the affected area is not malignant serving as a trigger that causes the at least one processor to discard the voice recorded by executing the recording control.

2. The diagnosis assistance device according to claim 1, further comprising:
a light source that illuminates the affected area with light, wherein the recording condition includes a condition that the light source is turned on.

3. The diagnosis assistance device according to claim 1, wherein the at least one processor is further configured to determine a type of malignancy of the affected area when the determination is made that the affected area is malignant, and associate a label with the voice and store the associated label in the memory, the label being a label expressing the determined type of the malignancy of the affected area.

4. The diagnosis assistance device according to claim 1, wherein the at least one processor is further configured to
further determine a type of benignancy of the affected area when a determination is made that the affected area is not malignant, and
associate a label with the voice and store the associated label, the label being a label expressing the determined type of benignancy of the affected area.

5. A diagnosis assistance method executed by at least one processor, the diagnosis assistance method comprising:
collecting voice around an affected area by at least one microphone;
executing image analysis software to determine, based on image data that is data of a captured image of the affected area, whether the affected area is malignant;
determining whether a recording condition is met;
executing recording control for controlling so that recording of the voice collected by the at least one microphone is started with the recording condition being met;
when a determination is made by the image analysis software that the affected area is malignant, storing in a memory the voice collected by the microphone and recorded by executing the recording control when the recording condition is met, the determination that the affected area is malignant serving as a trigger that causes the at least one processor to store the voice recorded by executing the recording control in the memory, and
when a determination is made by the image analysis software that the affected area is not malignant, discarding the voice recorded by executing the recording control when the recording condition is met, the determination that the affected area is not malignant serving as a trigger that causes the at least one processor to discard the voice recorded by executing the recording control.

6. A non-transitory computer readable recording medium storing a program causing a computer to implement functions of:
executing image analysis software to determine, based on image data that is data of a captured image of an affected area, whether the affected area is malignant;
determining whether a recording condition is met;
executing recording control for controlling so that recording of a voice collected around the affected area by at least one microphone is started with the recording condition being met;
when a determination is made by the image analysis software that the affected area is malignant, storing in a memory the voice collected by the at least one microphone and recorded by executing the recording control when the recording condition is met, the determination that the affected area is malignant serving as a trigger that causes the computer to implement the function of storing the voice recorded by executing the recording control in the memory, and
when a determination is made by the image analysis software that the affected area is not malignant, discarding the voice recorded by executing the recording control when the recording condition is met, the determination that the affected area is not malignant serving as a trigger that causes the at least one processor to discard the voice recorded by executing the recording control.

* * * * *

UNITED STATES PATENT AND TRADEMARK OFFICE
CERTIFICATE OF CORRECTION

| | |
|---|---|
| PATENT NO. | : 12,125,592 B2 |
| APPLICATION NO. | : 17/314166 |
| DATED | : October 22, 2024 |
| INVENTOR(S) | : Nobuhiro Aoki et al. |

It is certified that error appears in the above-identified patent and that said Letters Patent is hereby corrected as shown below:

In the Claims

Column 20, Claim 1, Line 52, delete "and".

Signed and Sealed this
Tenth Day of December, 2024

Katherine Kelly Vidal
*Director of the United States Patent and Trademark Office*